United States Patent
Suh et al.

(10) Patent No.: US 6,629,464 B2
(45) Date of Patent: Oct. 7, 2003

(54) LASER SHOCK PEENING QUALITY ASSURANCE BY ACOUSTIC ANALYSIS

(76) Inventors: Ui Won Suh, 10910 Allenhurst Blvd., Cincinnati, OH (US) 45241; James Douglas Risbeck, 7022 Butterwood Dr., Cincinnati, OH (US) 45241

(*) Notice: Subject to any disclaimer, the term of this patent is extended or adjusted under 35 U.S.C. 154(b) by 77 days.

(21) Appl. No.: 09/969,744

(22) Filed: Oct. 3, 2001

(65) Prior Publication Data

US 2003/0062349 A1 Apr. 3, 2003

(51) Int. Cl.$^7$ .................. G01N 29/06; G01N 21/63
(52) U.S. Cl. .................. 73/602; 73/11.02; 73/620; 73/643; 356/318
(58) Field of Search .................. 73/602, 579, 583, 73/598, 599, 600, 643, 645, 11.02, 587; 702/36, 39, 40

(56) References Cited

U.S. PATENT DOCUMENTS

| | | | |
|---|---|---|---|
| 3,850,698 A | | 11/1974 | Mallozzi et al. |
| 4,338,822 A | * | 7/1982 | Yamaguchi et al. ........ 73/643 |
| 4,386,526 A | * | 6/1983 | Roeder .................. 73/587 |
| 4,401,477 A | | 8/1983 | Clauer et al. |
| 4,937,421 A | | 6/1990 | Ortiz, Jr. et al. |
| 5,131,957 A | | 7/1992 | Epstein et al. |
| 5,492,447 A | | 2/1996 | Mannava et al. |
| 5,505,090 A | * | 4/1996 | Webster ................ 73/657 |
| 5,531,570 A | | 7/1996 | Mannava et al. |
| 5,569,018 A | | 10/1996 | Mannava et al. |
| 5,591,009 A | | 1/1997 | Mannava et al. |
| 5,674,328 A | | 10/1997 | Mannava et al. |
| 5,674,329 A | | 10/1997 | Mannava et al. |
| 5,681,490 A | | 10/1997 | Chang |
| 5,756,965 A | | 5/1998 | Mannava |
| 5,801,312 A | * | 9/1998 | Lorraine et al. ........... 73/602 |
| 5,948,293 A | | 9/1999 | Somers et al. |
| 5,951,790 A | | 9/1999 | Mannava et al. |
| 5,974,889 A | | 11/1999 | Trantow |
| 5,982,482 A | * | 11/1999 | Nelson et al. ......... 356/237.1 |
| 5,987,991 A | | 11/1999 | Trantow et al. |
| 6,075,593 A | | 6/2000 | Trantow et al. |
| 6,078,022 A | * | 6/2000 | Dulaney et al. ....... 219/121.85 |
| 6,191,385 B1 | | 2/2001 | O'Loughlin et al. |
| 6,254,703 B1 | | 7/2001 | Sokol et al. |
| 6,291,794 B1 | * | 9/2001 | Dulaney ............. 219/121.61 |

* cited by examiner

*Primary Examiner*—Hezron Williams
*Assistant Examiner*—Jacques Saint-Surin

(57) ABSTRACT

A method for quality control monitoring of laser shock peening a surface of a production workpiece during which laser beam pulses form a plurality of corresponding plasmas. An acoustic signal of each laser beam pulse during a period of time during a duration of each corresponding one of the plasmas is monitored and an acoustic energy parameter value for each of the acoustic signals for each of the corresponding laser pulses is calculated. A statistical function value of the workpiece based on the acoustic energy parameter values is calculated and compared to a pass or fail criteria for accepting or rejecting the workpiece. The criteria may be based on a pre-determined correlation of test piece statistical function data such as high cycle fatigue failure data of test pieces. The statistical function value may be an average of the acoustic energy parameter values of the laser beam pulses.

41 Claims, 7 Drawing Sheets

LASER SHOCK PEENING QUALITY ASSURANCE BY ACOUSTIC ANALYSIS

BACKGROUND OF THE INVENTION

1. Field of the Invention

This invention relates to quality assurance methods used for quality assurance for laser shock peening and, more particularly, for acoustic monitoring and statistical analysis method for quality assurance of a production laser shock peening process.

2. Discussion of the Background Art

Laser shock peening or laser shock processing, as it is also referred to, is a process for producing a region of deep compressive residual stresses imparted by laser shock peening a surface area of a workpiece. Laser shock peening typically uses multiple radiation pulses from high power pulsed lasers to produce shock waves on the surface of a workpiece similar to methods disclosed in U.S. Pat. No. 3,850,698, entitled "Altering Material Properties"; U.S. Pat. No. 4,401,477, entitled "Laser Shock Processing"; and U.S. Pat. No. 5,131,957, entitled "Material Properties". Laser shock peening, as understood in the art and as used herein, means utilizing a laser beam from a laser beam source to produce a strong localized compressive force on a portion of a surface by producing an explosive force by instantaneous ablation or vaporization of a painted or coated or uncoated surface. Laser peening has been utilized to create a compressively stressed protection layer at the outer surface of a workpiece which is known to considerably increase the resistance of the workpiece to fatigue failure as disclosed in U.S. Pat. No. 4,937,421, entitled "Laser Peening System and Method". These methods typically employ a curtain of water flowed over the workpiece or some other method to provide a confining medium to confine and redirect the process generated shock waves into the bulk of the material of a component being LSP'D to create the beneficial compressive residual stresses. Other techniques to confine and redirect the shock waves that do not use water have also been developed.

Laser shock peening is being developed for many applications in the gas turbine engine field, some of which are disclosed in the following U.S. Pat. Nos. 5,756,965 entitled "ON THE FLY LASER SHOCK PEENING"; U.S. Pat. No. 5,591,009, entitled "Laser shock peened gas turbine engine fan blade edges"; U.S. Pat. No. 5,569,018, entitled "Technique to prevent or divert cracks"; U.S. Pat. No. 5,531,570, entitled "Distortion control for laser shock peened gas turbine engine compressor blade edges"; U.S. Pat. No. 5,492,447, entitled "Laser shock peened rotor components for turbomachinery"; U.S. Pat. No. 5,674,329, entitled "Adhesive tape covered laser shock peening"; and U.S. Pat. No. 5,674,328, entitled "Dry tape covered laser shock peening", all of which are assigned to the present Assignee. These applications, as well as others, are in need of efficient quality assurance testing during production runs using laser shock peening.

LSP is a deep treatment of the material and it is desirable to have a quality assurance test that is indicative of a volumetric LSP effect. It is also desirable to have a QA method that is compatible with a dual sided or simultaneous dual sided LSP process wherein substantially equal compressive residual stresses are imparted to both sides of a workpiece, i.e. along the leading edge of a gas turbine engine fan blade.

One laser shock peening quality assurance technique previously used is high cycle fatigue (HCF) testing of blades having leading edges which are LSP'd and notched in the LSP'd area before testing. This method is destructive of the test piece, fairly expensive and time consuming to carry out, and significantly slows production and the process of qualifying LSP'd components. An improved quality assurance method of measurement and control of LSP that is a non-destructive evaluation (NDE), inexpensive, accurate, quick, and easy to set up is highly desirable. It is also desirable to have a real time NDE quality assurance method that is relatively inexpensive and sufficiently economical to be used on each workpiece instead of a sampling of workpieces. LSP is a process that, as any production technique, involves machinery and is time consuming and expensive. It is desirable to have a real time NDE method so that process deviations can be discovered during a production run. Therefore, any real time techniques that can reduce the amount or complexity of production machinery and/or production time are highly desirable.

Interferometric profilometry method and apparatus to obtain volumetric data of a single laser shock peened test dimple created with a single firing of a laser used in the laser shock peening process is disclosed in U.S. Pat. No. 5,948,293 "Laser shock peening quality assurance by volumetric analysis of laser shock peened dimple". Other QA methods are disclosed in U.S. Pat. No. 5,987,991 "Determination of Rayleigh wave critical angle"; U.S. Pat. No. 5,974,889 "Ultrasonic multi-transducer rotatable scanning apparatus and method of use thereof"; and U.S. Pat. No. 5,951,790 "Method of monitoring and controlling laser shock peening using an in plane deflection test coupon". U.S. Pat. No. 6,254,703,entitled "Quality Control Plasma Monitor for Laser Shock Processing" discloses a method and apparatus for quality control of laser shock processing by measuring emissions and characteristics of a workpiece when subjected to a pulse of coherent energy from a laser. These empirically measured emissions and characteristics of the workpiece are correlated to theoretical shock pressure, residual stress profile, or fatigue life of the workpiece. Apparatus disclose includes a radiometer or acoustic detection device for measuring these characteristics.

SUMMARY OF THE INVENTION

A method for quality control testing or monitoring of the laser shock peening process of production workpieces includes the following steps. Step (a) includes laser shock peening a surface of the production workpiece by firing a plurality of laser beam pulses from a laser shock peening apparatus on the surface of the production workpiece and forming a plurality of corresponding plasmas. Each one of the plasmas for each one of the pulses has a duration in which the plasma causes a region to form beneath the surface. The region has deep compressive residual stresses imparted by the laser shock peening process. Step (b) includes measuring acoustic signal for each of the laser beam pulses during a period of time during the duration of each corresponding one of the plasmas. Step (c) includes calculating an acoustic energy parameter value for each of the acoustic signals for each of the corresponding laser pulses or plasmas. Step (d) includes calculating a statistical function value of the workpiece based on the acoustic energy parameter values. The statistical function value may be an average of the acoustic energy parameter values for the plurality of the laser beam pulses. In step (e) the statistical function value is compared to a pass or fail criteria for quality assurance of the laser shock peening process for accepting or rejecting the workpiece. Besides using the averages of the acoustic energy parameter values to determine the statistical function values other types of statistical functions and analysis may be used, i.e. analysis and functions using regression or standard deviations.

The pass or fail criteria may be based on a pre-determined correlation of test piece statistical function data. More particular embodiments use high cycle fatigue failure based on high cycle fatigue tests of test pieces. The test pieces may have a failure precipitating flaw within a laser shock peened area of the test piece that was laser shock peened in the same or similar laser shock peening apparatus.

Two exemplary types of acoustic signal monitoring devices are disclosed. The first type is an acoustic transducer mounted to the workpiece, which detects acoustic signals though the workpiece. The second type is a microphone located away from the workpiece, which detects airborne acoustic signals. The acoustic signals may be used to calculate various types of acoustic energy parameters of the laser pulse or plasma. One exemplary type of acoustic energy parameter is a maximum amplitude of each corresponding one of the signals during the duration of each corresponding one of the plasmas. A second exemplary type of acoustic energy parameter is a signal from one of the plasmas integrated over time of a sample period of the duration of the plasma and also referred to as the area under the curve of the acoustic signal. The exemplary embodiments describe four separate and distinct acoustic energy parameters that can be calculated during laser shock peening of production workpieces and four corresponding statistical function values that can be correlated to pass or fail criteria based on the same parameters of test pieces.

The surface is typically laser shock peened with more than one sequence of coatings of the surface and then firings of the laser beams on the surface such that adjacent laser shock peened circular spots are hit in different sequences or passes of the laser beams forming layers of overlapping laser shock peening spots. The pattern of sequences entirely covers the laser shock peened surface. The plurality of laser beam pulses or plasmas used in the present invention may be from all or a portion of all of the pulses or plasmas in each layer for the purposes of correlation. Not all of the laser beam pulses or plasmas need be included in the plurality of the laser beam pulses used for the quality assurance method of the present invention. Acoustic data from a portion of the plasmas may be used for the plurality of the laser beam pulses used in method.

The present invention provides efficient, reliable, and repeatable quality assurance testing during laser shock peening production runs. The invention provides a quality assurance method of measurement and control of LSP that is a non-destructive evaluation (NDE), inexpensive, accurate, quick, and easy to set up. The method of the present invention provides a real time NDE quality assurance method that is relatively inexpensive and sufficiently economical to be used on each workpiece instead of a sampling of workpieces. The real time NDE method of the present invention allows deviations to be discovered during a production run resulting in lower scrap rates and less wasted production time.

BRIEF DESCRIPTION OF THE DRAWINGS

The foregoing aspects and other features of the invention are explained in the following description, taken in connection with the accompanying drawings where.

DETAILED DESCRIPTION

Figure 1:
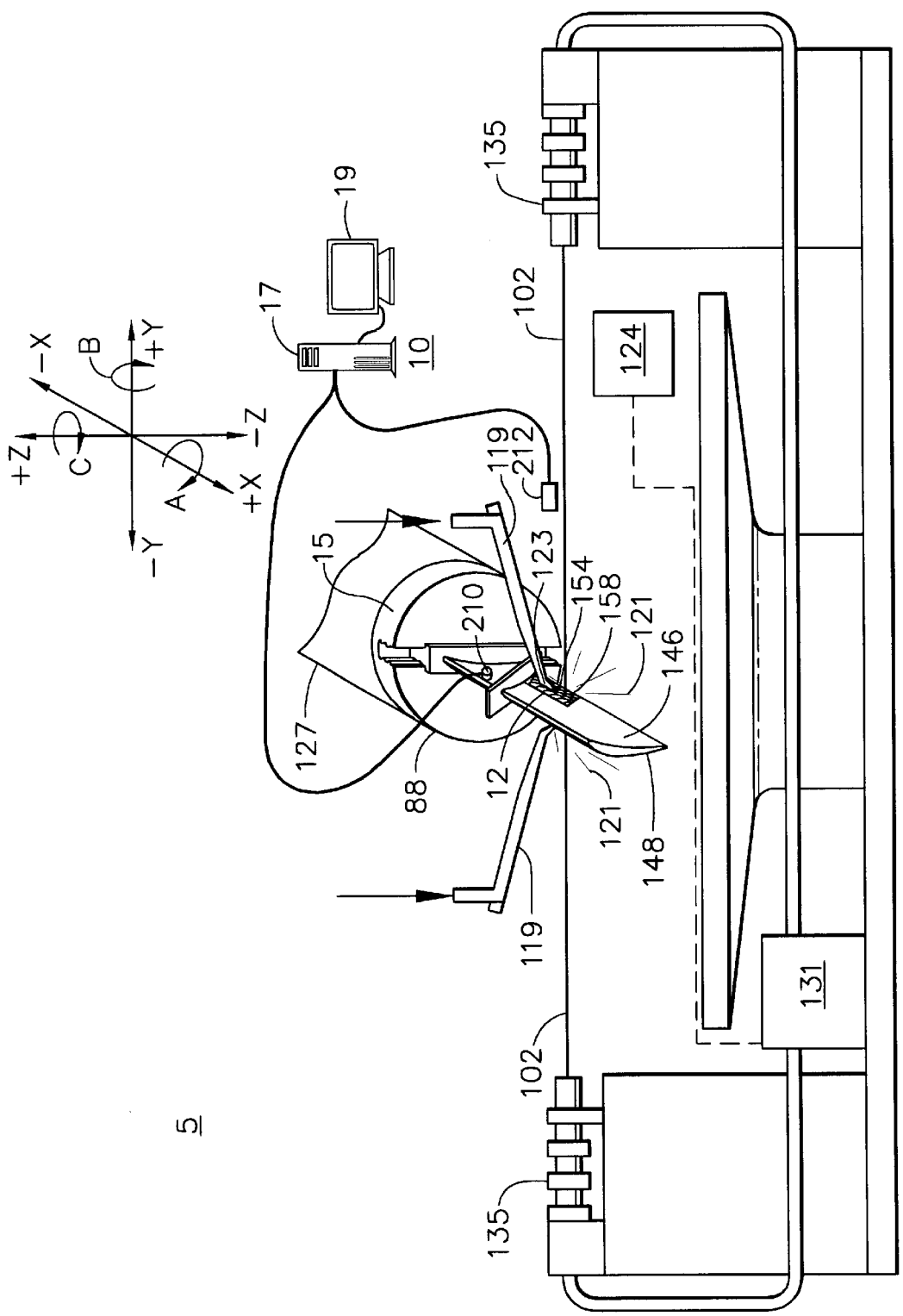
FIG. 1 is a diagrammatic illustration of a laser shock peening system with an acoustic monitoring system for quality assurance of a production laser shock peening process in an exemplary embodiment of the method of the present invention.

Quality assurance is typically a go or no go, pass or fail, accept or reject type of analysis. The method and techniques of the present invention involves quality assurance of the laser shock peening process on a production workpiece such as an exemplary aircraft turbofan gas turbine engine production fan blade 108 illustrated in FIGS. 1, 2, and 5. Illustrated in FIG. 1 is a diagrammatic representation of a laser shock peening system 5 having an acoustic monitoring system 10. The laser shock peening system 5 has a conventional laser beam generator 131 with an oscillator, a pre-amplifier, a beam splitter which feeds the pre-amplified laser beam into two beam optical transmission circuits each having a first and second amplifier, and optics 135 which include optical elements that transmit and focus the laser beams 102 on the coated surfaces of the blade 108. The acoustic monitoring system 10 is used to perform a quality assurance method for quality control of a laser shock peening process. The methods and apparatus of the present invention involves quality assurance of a laser shock peening process on a production workpiece such as an exemplary aircraft turbofan gas turbine engine fan blade 108 or other object made of a metallic material as disclosed in U.S. Pat. Nos. 5,492,447, 5,674,329, 5,674,328, and 5,591,009. The methods of the present invention are tests performed during laser shock peening of each workpiece. During production runs, one or more functions of acoustic signal data is compared to pre-determined pass/fail criteria such as a high cycle fatigue correlation for passing or failing the workpieces.

The laser shock peening system 5 for laser shock peening the fan blade 108 is illustrated with the fan blade 108 mounted in a fixture 15 which is attached to a five-axis computer numerically controlled (CNC) manipulator 127. Five axes of motion illustrated in the exemplary embodiment are conventional translational axes X, Y, and Z, and conventional rotational axes A, B and C which are well known in CNC machining. The manipulator 127 moves and positions the production fan blades 108 and test blades 109 to effect laser shock peening on the fly. Laser shock peening may be done in a number of various ways using paint or tape as an ablative medium (see U.S. Pat. No. 5,674,329 entitled "Adhesive Tape Covered Laser Shock Peening"). The same laser shock peening system 5 is used in the laser shock peening process of the leading edge section 150 of the production fan blade 108 and the test fan blades 109 (representing the test pieces and workpieces).

Figure 5:
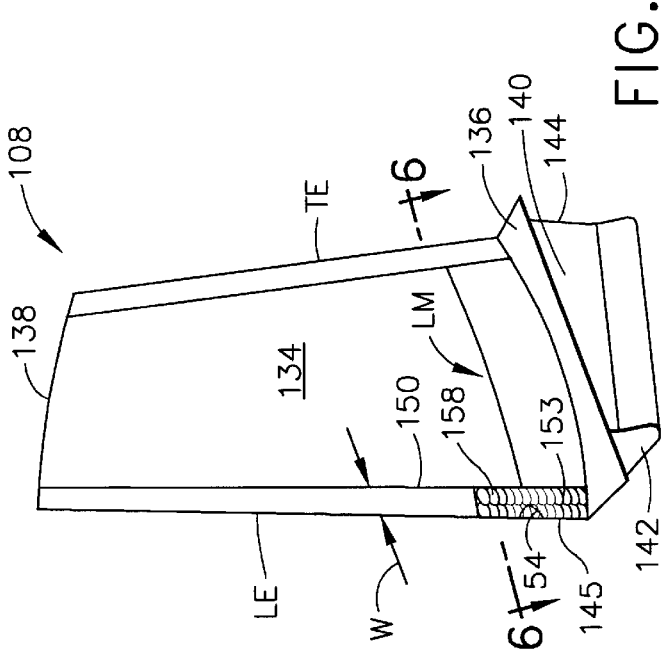
FIG. 5 is a perspective view illustration of a laser shock peened blade exemplifying a workpiece in the exemplary embodiment of the present invention.
Figure 6:
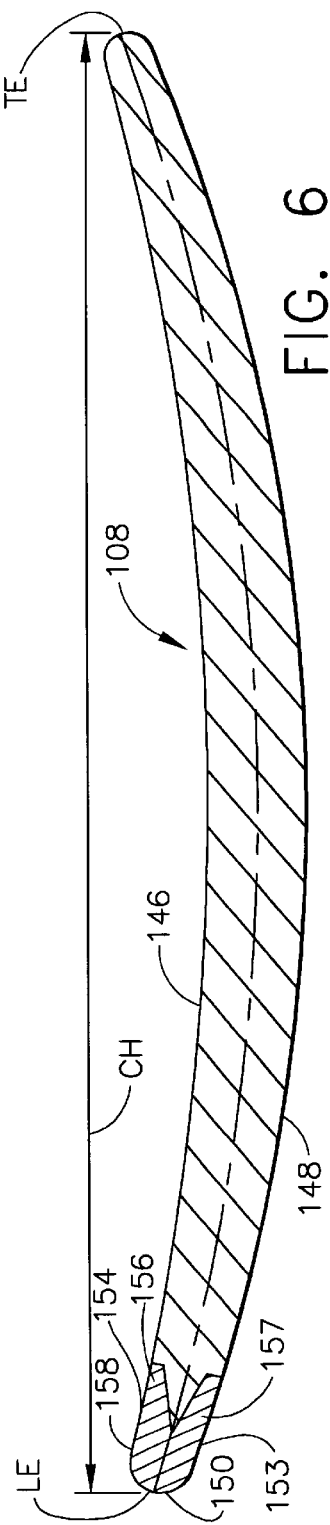
FIG. 6 is a cross-sectional view illustration of the fan blade through 6—6 in FIG. 5.

Referring to FIGS. 5 and 6, the production fan blade 108 includes an airfoil 134 extending radially outward from a blade platform 136 to a blade tip 138 and a root section 140 extending radially inward from the platform 136. The root section 140 has a blade root 142 connected to the platform 136 by a blade shank 144. The airfoil 134 extends in a chordwise direction between a leading edge LE and a trailing edge TE of the airfoil. The fan blade 12 has a leading edge section 150 that extends along the leading edge LE of the airfoil 134 from the blade platform 136 to the blade tip 138. The airfoil 134 has a pressure side 146 and a suction side 148 extending between the leading edge and trailing edges LE and TE of the airfoil. A chord CH of the airfoil 134 extends between the leading LE and trailing edge TE at each cross-section of the blade as illustrated in FIG. 6. The leading edge section 150 includes a pre-determined first width W such that the leading edge section 150 encompasses an area where nicks 54 and tears that may occur along the leading edge of the airfoil 134 during engine operation. The airfoil 134 subject to a significant tensile stress field due to centrifugal forces generated by the fan blade 108 rotating during engine operation. The airfoil 134 is also subject to vibrations generated during engine operation and the nicks 54 and tears operate as high cycle fatigue stress risers producing additional stress concentrations around them.

To counter fatigue failure of portions of the blade along possible crack lines that can develop and emanate from the nicks and tears, a laser shock peened patch 145 is placed along a portion of the leading edge LE where incipient nicks and tears may cause a failure of the blade due to high cycle fatigue. Laser shock peening produces laser shock peening spots 158 within the laser shock peened patch 145. In the exemplary embodiment of the invention illustrated herein, the pressure side 146 and the suction side 148 are simultaneously laser shock peened to form pressure side and suction side laser shock peened surfaces 153 and 154 and corresponding pressure side and suction side pre-stressed regions 155 and 156, respectively, having deep compressive residual stresses imparted by laser shock peening (LSP) extending into the airfoil 134 from the laser shock peened surfaces as seen in FIG. 6. The pre-stressed regions are illustrated along only a portion of the leading edge section 150 but may extend along the entire leading edge LE or longer portion thereof if do desired. The pre-determined criteria of the exemplary embodiment is based on a correlation of one or more functions of ultrasonic intensity data versus high cycle fatigue data of test versions of the workpieces that are exemplified by laser shock peened and notched test fan blades 109 having a notch 152 illustrated in FIG. 7. In the exemplary embodiments of the invention, the production and test fan blades 108 and 109, respectively, are laser shock peened the same way during production runs and HCF testing runs for the correlation.

Figure 7:
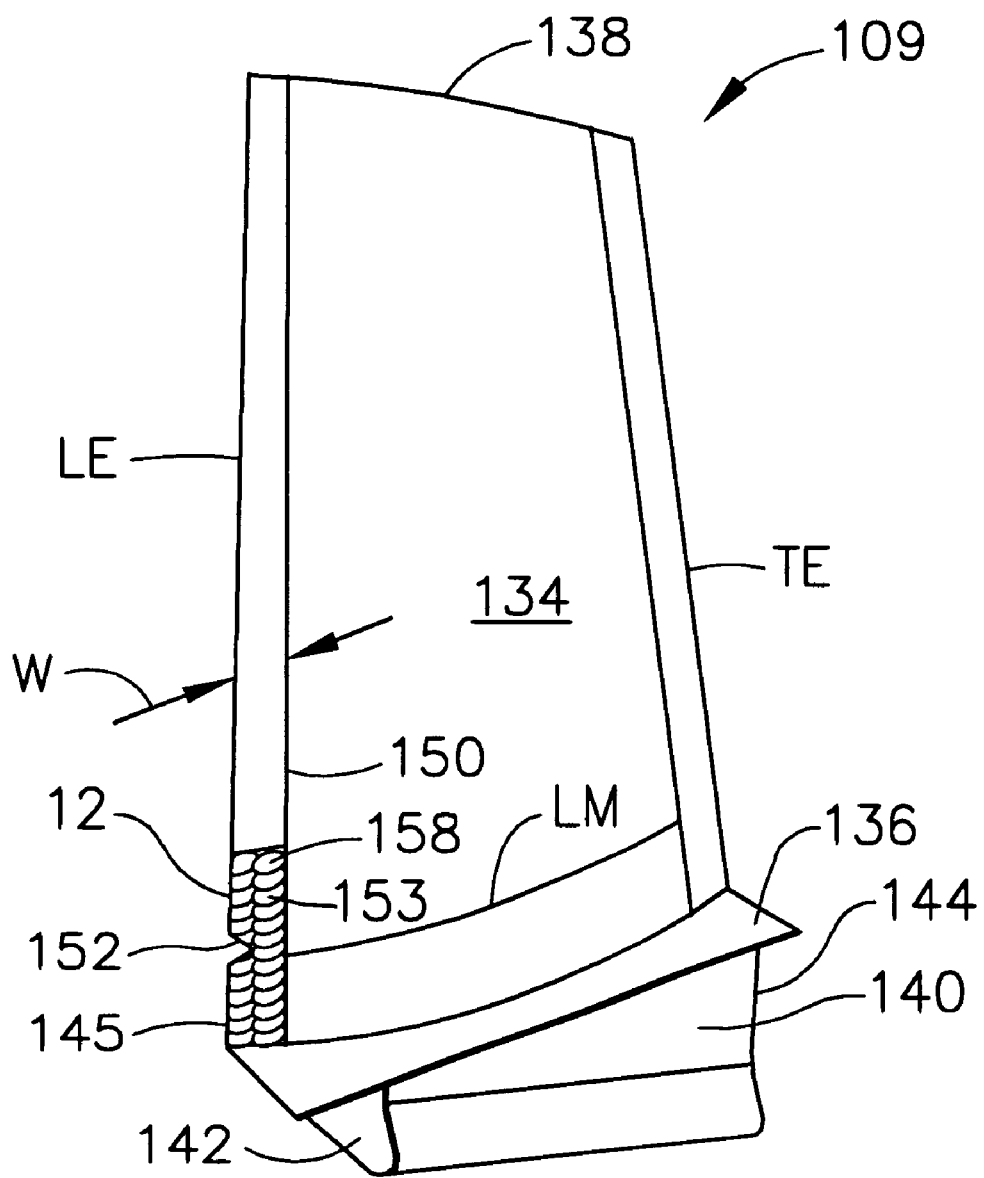
FIG. 7 is a perspective view illustration of a laser shock peened blade with a notch exemplifying test piece corresponding to the workpiece illustrated in FIG. 5 which is used to determine a correlation between high cycle fatigue failure and exemplary statistical functions of the present invention.

The high cycle fatigue (HCF) correlation of the test fan blades 109 in the exemplary embodiments of the invention is based on fatigue testing of the laser shock peened and notched test fan blades 109 as illustrated in FIG. 7. The test fan blades 109 are full scale and notched to precipitate a failure. The test pieces or test fan blades 109 are made the same way as the actual production fan blades 108 with a notch 152 added after the test blade 109 is laser shock peened to form the patch 145.

The laser shock peened test fan blades 109 are acoustically monitored and the signals are statistically analyzed in the same manner as the production blades 108. The HCF testing may be used to establish pass/fail criteria for use during production runs to be compared to the results of the statistical analysis from the acoustic monitoring and statistical analysis of the acoustic data. The laser shock peened test fan blades 109 are vibrated at its first mode frequency until it fails. A number of test fan blades 109 or just one test blade 109 may be notched and subjected to high cycle fatigue tests to establish the correlation. For high cycle fatigue, each laser shock peened test fan blade 109 has a notch 152, representing a failure precipitating flaw, placed in the laser shock peened patch 145. The notch 152 is placed at a pre-determined position of the pre-stressed regions 155 and 156 after the blade is laser shock peened. The notch 152 may be centered about a pre-determined mode line such as a first mode line LM. If tested blade meets standards or test criteria on length of time and amplitude of the forcing function that is exiting the blade, then it is acceptable. These results can then be used during production runs to continuously monitor quality of the laser shock peening process. The process may be stopped and the laser shock peening system may be based on the statistical analysis of the acoustic data fixed and/or the production part may be scrapped or pulled out of the line for further analysis later.

Referring to FIG. 1, the fan blade 108 is mounted in the fixture 15 which is attached to a five-axis computer numerically controlled (CNC) manipulator 127. Five axes of motion illustrated in the exemplary embodiment are conventional translational axes X, Y, and Z, and conventional rotational axes A and C which are well known in CNC machining. The manipulator 127 moves and positions the production and test production fan blades 108 and 109 to effect laser shock peening on the fly. Laser shock peening may be done in a number of various ways using paint or tape as an ablative medium (see U.S. Pat. No. 5,674,329 entitled "Adhesive Tape Covered Laser Shock Peening"). The same laser shock peening system 5 is used in the laser shock peening process of the leading edge section 150 of the production fan blade 108 and the test fan blades 109 (representing the test pieces and workpieces).

The area to be laser shock peened and form the laser shock peened patch 145, the pressure and suction side laser shock peened surfaces 153 and 154 are covered with an ablative coating such as paint or adhesive tape to form a coated surface as disclosed in U.S. Pat. Nos. 5,674,329 and 5,674,328. The coating provides an ablative medium over which is a clear containment medium which may be a clear fluid curtain such as a curtain of flowing water 121.

The laser beam shock induced deep compressive residual stresses may be produced by repetitively firing two high power laser beams 102, each of which is defocused±a few mils with respect to the coated pressure side and suction side laser shock peened surfaces 153 and 154 of the pressure side 146 and the suction side 148 of the production fan blade 108. Each of the laser beams is fired through the curtain of flowing water 121 supplied by a conventional water nozzle 123 at the end of a conventional water supply tube 119. The curtain of flowing water 121 is flowed over the coated surfaces. The coating is ablated generating plasma which results in shock waves on the surface of the material. Other ablative materials may be used to coat the surface as suitable alternatives to paint. These coating materials include metallic foil or adhesive plastic tape as disclosed in U.S. Pat. Nos. 5,674,329 and 5,674,328. These shock waves are re-directed towards the coated surfaces by the curtain of flowing water 121 to generate travelling shock waves (pressure waves) in the material below the coated surfaces. The amplitude and quantity of these shock waves determine the depth and intensity of compressive stresses. The ablative coating is used to protect the target surface and also to generate plasma. The ablative coating is used to protect the target surface and also to generate plasma. The laser beam shock induced deep compressive residual stresses in the compressive pre-stressed regions are generally about 50–150 KPSI (Kilo Pounds per Square Inch) extending from the laser shock peened surfaces to a depth of about 20–50 mils into the pre-stressed regions. Low powered laser beams of 3–10 joules or even perhaps 1–10 joules may be used with circularly shaped laser shock peening spots 158 having a diameter of about 8 mm. Other shapes for the laser shock peening spots 158 may be used. By way of example oblique circular cross-section laser beams produce elliptically shaped laser shock peening spots 158 which may also be used in the present invention.

The production fan blade 108 is continuously moved while the stationary high power laser beams 102 are continuously firing through the curtain of flowing water 121 on the coated pressure and suction side laser shock peened surfaces 153 and 154 and forming spaced apart circular laser shock peened spots 158. The production fan blades 108 are laser shock peened the same way during production runs and HCF testing runs for the correlation. A controller 124 is be used to modulate and control the laser shock peening system 5 to fire the laser beams 102 on the coated surfaces in a controlled manner. Ablated coating material is washed out by the curtain of flowing water 121.

Figure 3:
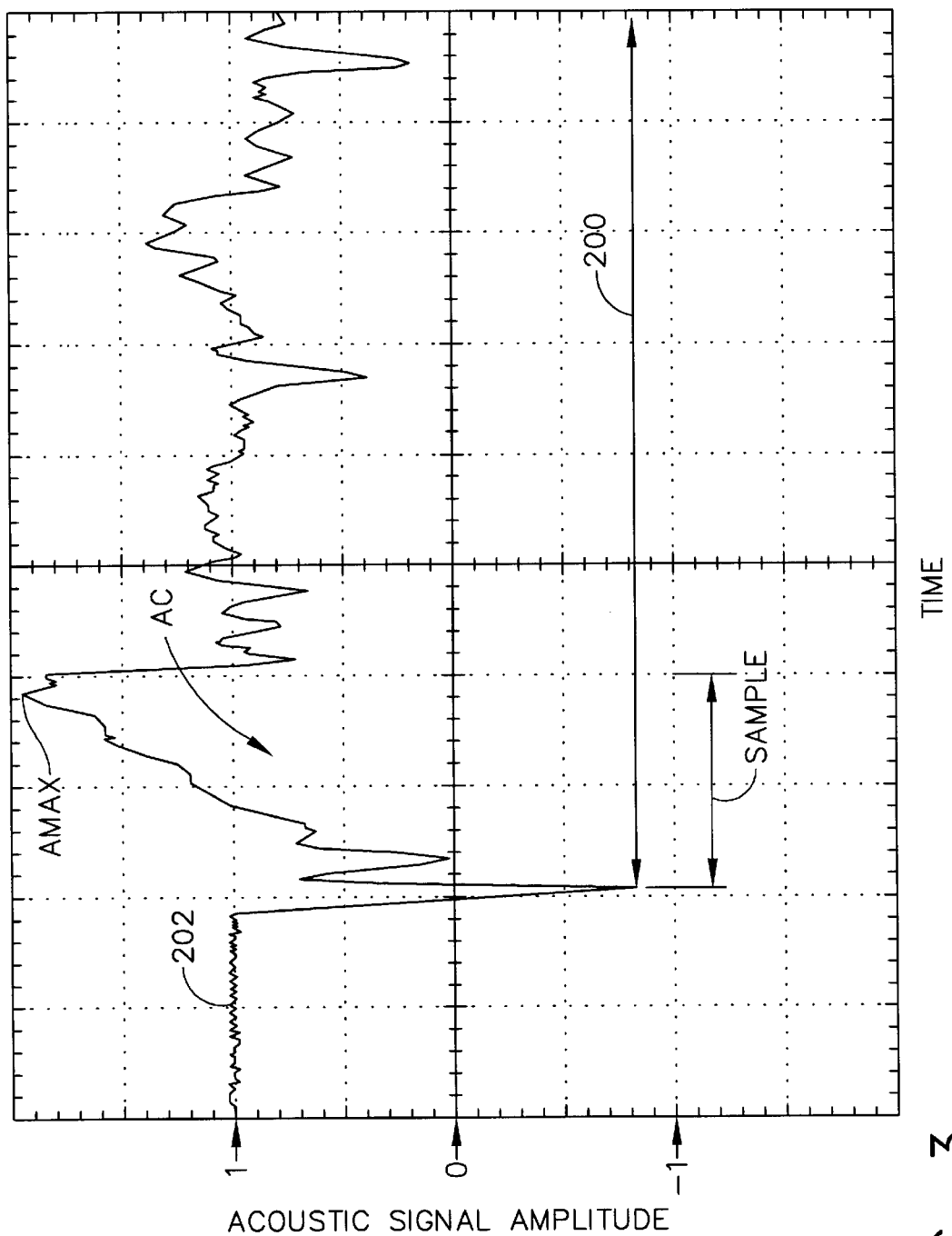
FIG. 3 is an illustration of a screen depicting an acoustic signal from a plasma of a laser pulse during the laser shock peening process.

The method for quality control testing or monitoring of the laser shock peening process of production workpieces 108 includes the following steps. Step (a) includes laser shock peening a surface 153 of the production workpiece 108 by firing a plurality of laser beam 102 pulses from a laser shock peening system 5 on the surface 153 of the production workpiece and forming a plurality of corresponding plasmas. Each one of the plasmas for each one of the pulses has a duration 200 in which the plasma causes a region 157 to form beneath the surface. The region 157 has deep compressive residual stresses imparted by the laser shock peening process. In step (b) an acoustic signal 202 as illustrated in FIG. 3 is measured for each of the laser beam pulses during a period of time during the duration of each corresponding one of the plasmas as illustrated by a sample period. In step (c) an acoustic energy parameter value for each of the acoustic signals for each of the corresponding laser pulses or plasmas is calculated. In step (d) a statistical function value of the workpiece based on the acoustic energy parameter values is calculated. The statistical function value may be an average of the acoustic energy parameter values for the plurality of the laser beam pulses. In step (e) the statistical function value is compared to pass or fail criteria for quality assurance of the laser shock peening process for accepting or rejecting the workpiece. The pass or fail criteria may be based on a pre-determined correlation of test piece statistical function data. More particular embodiments use high cycle fatigue failure based on high cycle fatigue tests of test pieces such as the test blade 109 that were laser shock peened in the same or similar laser shock peening system 5 as the workpieces represented by production blade 108. Furthermore, the test pieces may have a failure precipitating flaw within a laser shock peened area of the test piece that was laser shock peened in the same or similar laser shock peening apparatus.

Figure 2:
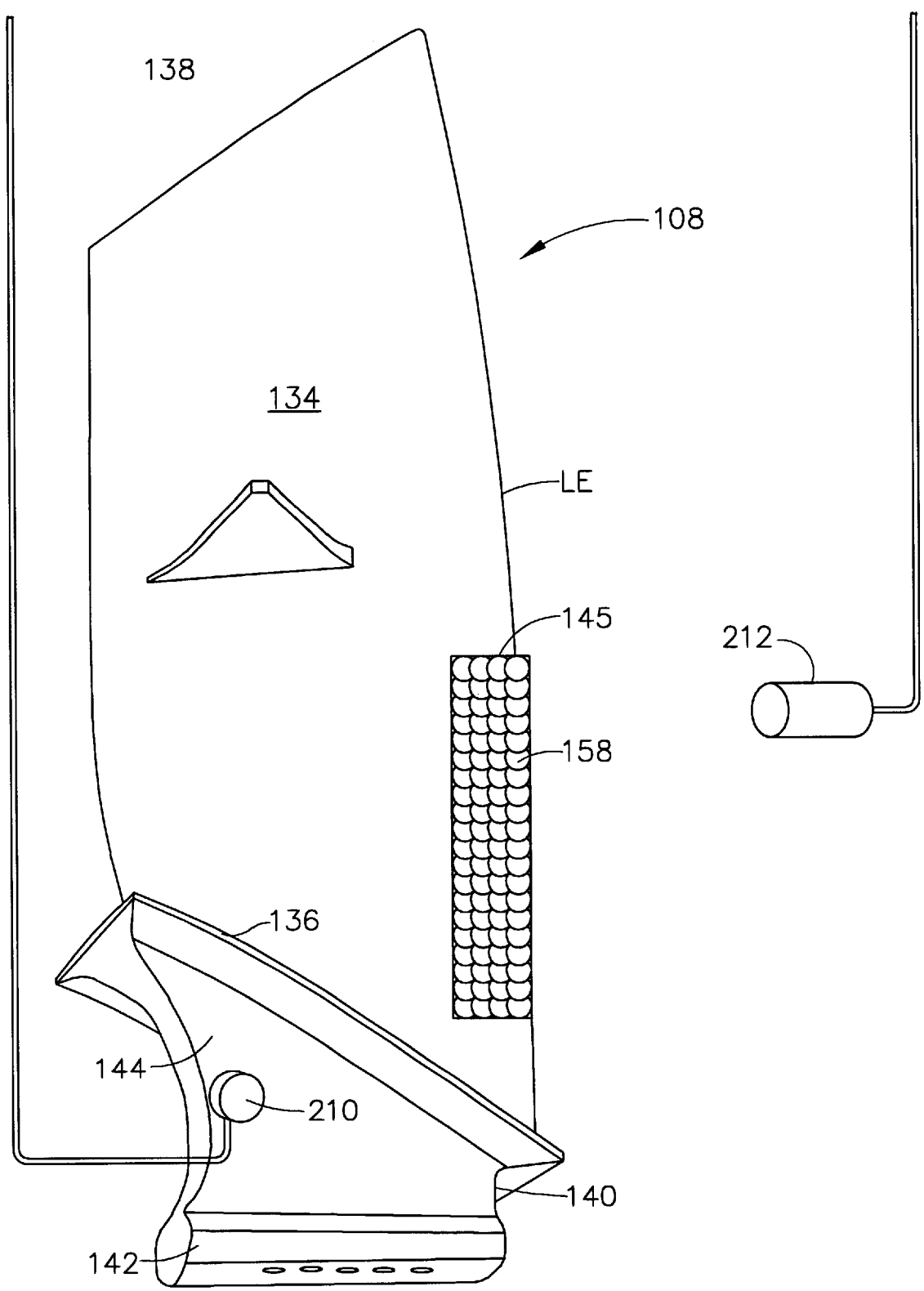
FIG. 2 is a perspective view illustration of a production fan blade exemplifying a laser shock peened production workpiece and acoustic energy monitoring devices used in the exemplary embodiment of the present invention.

The embodiments of the method of the invention explained above are for using a single acoustic signal motoring device for monitoring a single plurality of acoustic signals resulting in a corresponding single plurality of acoustic energy parameter values used to calculate a single statistical function value. Two types of acoustic signal motoring devices are illustrated in FIGS. 1 and 2. The first type is an acoustic transducer 210 mounted to the workpiece 108 which detects acoustic signals though the workpiece. The second type is a microphone 212 located away from the workpiece and which detects airborne acoustic signals. The acoustic signals may be used to calculate various types of acoustic energy parameters of the laser pulse or plasma. Acoustic signal data from the acoustic transducer 210 and the microphone 212 are transmitted to a computer 17 for analysis of the data. A monitor 19 of the computer 17 can be used to display the data and results of statistical analysis of the data. The acoustic energy parameter values for each of the acoustic signals for each of the corresponding laser pulses or plasmas may also be displayed on the screen as well as the calculated statistical function values of the workpiece based as compared to the pass or fail criteria for quality assurance of the laser shock peening process for accepting or rejecting the workpiece. Referring to FIG. 3, one exemplary type of acoustic energy parameter is a maximum amplitude AMAX of each corresponding one of the signals during the duration of each corresponding one of the plasmas. A second exemplary type of acoustic energy parameter is a signal from one of the plasmas integrated over time of a sample period of the duration 200 of the plasma illustrated as the area under the curve AC of the acoustic signal 202 in FIG. 3. The are under the curve AC includes negative values for portions of the signal in the sample period that have negative values. The exemplary embodiments therefore describe four separate and distinct acoustic energy parameters that can be calculated during laser shock peening of production workpieces and a corresponding number of statistical function values that can be correlated to pass or fail criteria based on the same parameters of test pieces. In the present invention, any of the four can be used separately or together to provide the quality assurance for laser shock peening process.

The present invention provides efficient, reliable, and repeatable quality assurance testing during production runs using laser shock peening. The real time NDE method of the present invention allows deviations to be discovered during a production run resulting in lower scrap rates and less wasted production time. The use of both the airborne and part-borne acoustic data from the microphone and workpiece mounted acoustic transducer respectively allows monitoring of different laser shock peening parameters. It is expected that part-borne acoustic signal is a more discriminating signal and is suitable to monitor laser shock peening conditions related to water confinement layer, coating, laser quality, and optical path. It is also expected that airborne acoustic signal is suitable to monitor laser shock peening conditions related to water confinement layer, coating, laser quality, and optical path.

Figure 4:
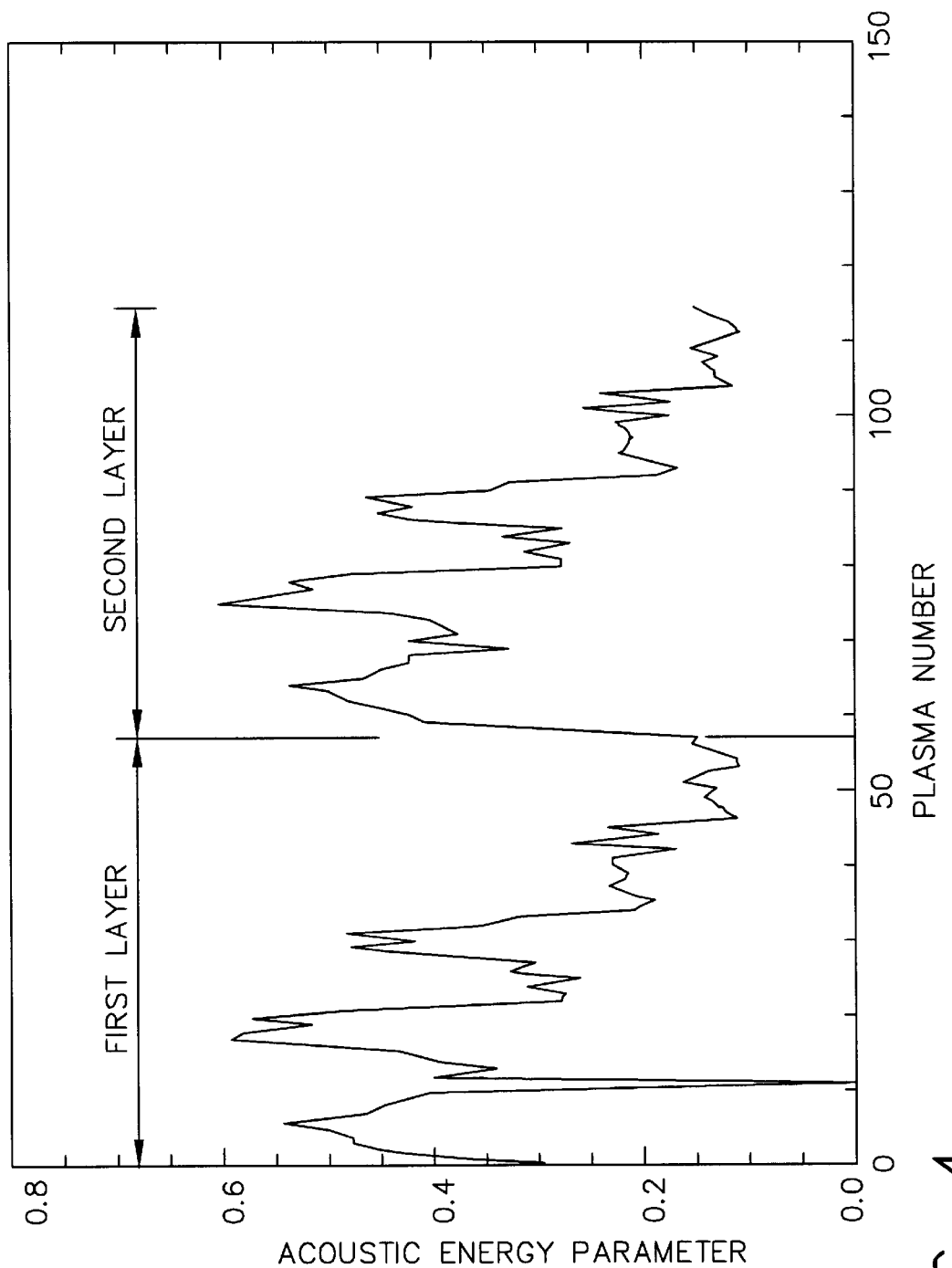
FIG. 4 is an illustration of a screen depicting a plot of acoustic energy parameters from acoustic signals from first and second pluralities of plasmas of laser pulses during the laser shock peening process producing first and second layers of laser shock peening spots.
Figure 8:
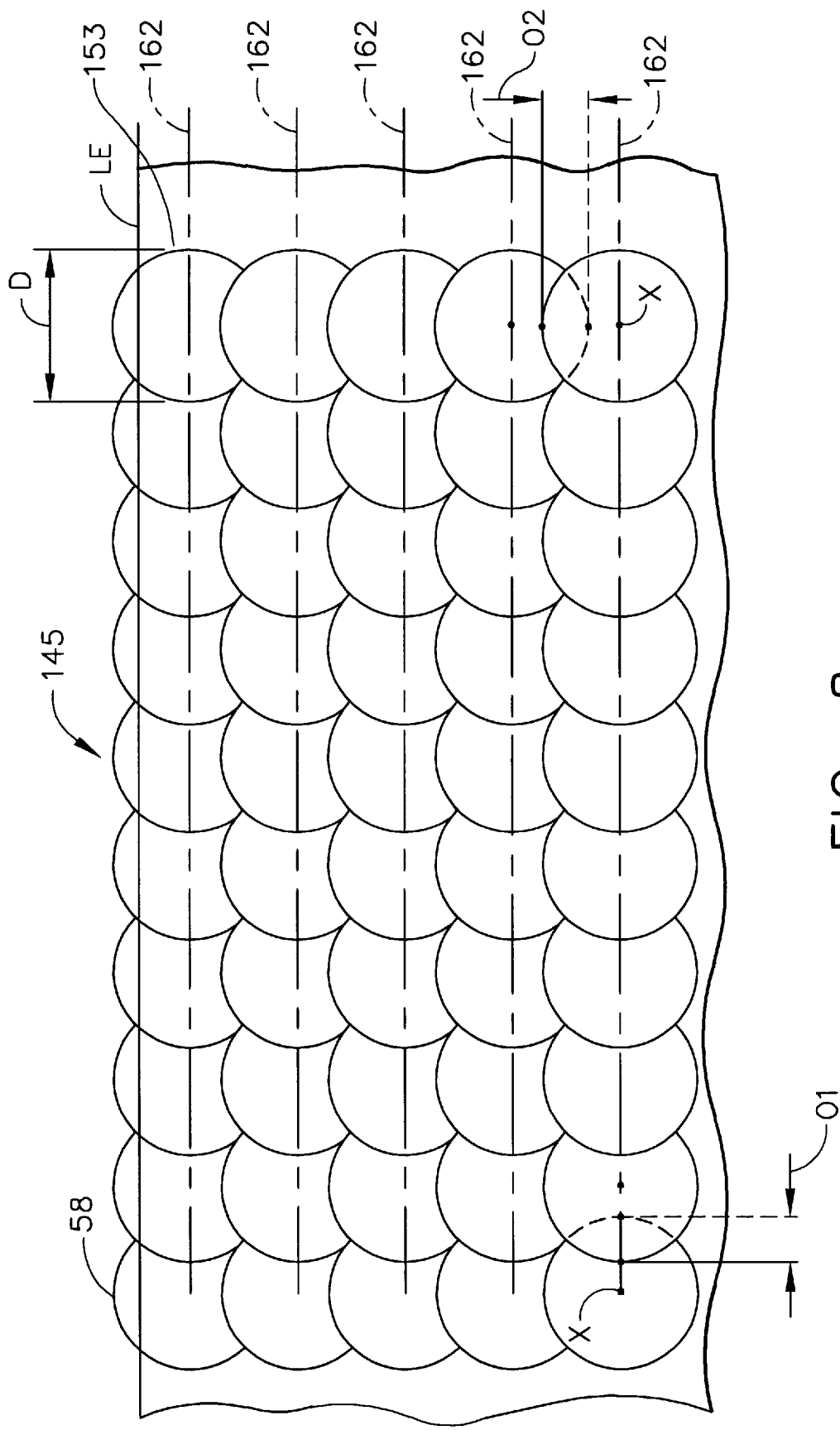
FIG. 8 is a diagrammatic side view illustration of a pattern of circular laser shock peened spots formed in first and second layers of the exemplary laser shock peening process.

The signals used are from a plurality of laser beam 102 pulses. The exemplary embodiment uses data from all the pulses illustrated as laser shock peening spots 158 on the laser shock peened surface 153 in FIG. 8. The surface is typically laser shock peened with more than one sequence of coatings of the surface and then firings of the laser beams on the surface such that adjacent laser shock peened spots are hit in different sequences or passes of the laser beams forming layers of overlapping laser shock peening spots 158. The pattern of sequences entirely covers the laser shock peened surface 153. The circular laser shocked peened spots 158 have a diameter D in a row 162 of overlapping laser shock peened spots. A first overlap is between adjacent circular laser shock peened spots 158 in a given row and is generally defined by a first offset O1 between centers X of the adjacent laser shock peened spots 158 and can vary from about 30%–50% or more of the diameter D. A second overlap is between adjacent laser shock peened spots 158 in adjacent rows and is generally defined by a second offset O2 between adjacent row centerlines 162 and can vary from about 30%–50% of the diameter D depending on applications and the strength or fluency of the laser beam. Illustrated in FIG. 4 is an example of acoustic energy data as represented by the acoustic energy parameter values for each of the acoustic signals for each of the corresponding laser pulses for two layers of laser shock peening spots 158. Illustrated in FIG. 4 is a plot of the acoustic energy parameter values for two passes of the laser beams 102 or two layers of laser shock peening spots 158 in which by way of example each layer has 58 laser shock peening spots 158. Not all of the laser beam pulses or plasmas need be included in the plurality of the laser beam pulses used for the quality assurance method of the present invention. Acoustic data from a portion of the plasmas may be used for the plurality of the laser beam pulses used in method. Besides using the averages of the acoustic energy parameter values to determine the statistical function values other types of statistical functions and analysis may be used, i.e. analysis and functions using regression or standard deviations.

The embodiment of the method of the present invention illustrated herein includes continuously moving the blade while continuously firing the laser beam on the taped surface and adjacent laser shock peened spots may be hit in different sequences. However, the laser beam may be moved instead just so long as relative movement between the beam and the surface is effected.

While there have been described herein what are considered to be preferred and exemplary embodiments of the present invention, other modifications of the invention shall be apparent to those skilled in the art from the teachings herein and, it is therefore, desired to be secured in the appended claims all such modifications as fall within the true spirit and scope of the invention. Accordingly, what is desired to be secured by Letters Patent of the United States is the invention as defined and differentiated in the following claims.

We claim:
1. A method for quality control testing of a laser shock peening process of production workpieces, said method comprising the following steps:
(a) laser shock peening a surface of the production workpiece by firing a plurality of laser beam pulses from a laser shock peening system on the surface of the production workpiece and forming a plurality of corresponding plasmas, each one of the plasmas for each one of the pulses having a duration in which the plasma causes a region to form beneath the surface, the region having deep compressive residual stresses imparted by the laser shock peening process,
(b) measuring an acoustic signal for each of the laser beam pulses during a period of time during the duration of each corresponding one of the plasmas,
(c) calculating an acoustic energy parameter value for each of the acoustic signals,
(d) calculating a statistical function value of the workpiece based on the acoustic energy parameter values, and
(e) comparing the statistical function value to a pass or fail criteria for quality assurance of the laser shock peening process for accepting or rejecting the workpiece.
2. A method as claimed in claim 1 wherein the pass or fail criteria is based on a pre-determined correlation of test piece statistical function data and high cycle fatigue failure based on high cycle fatigue tests of test pieces that were laser shock peened in the same or similar laser shock peening apparatus.
3. A method as claimed in claim 2 wherein the test pieces each have a failure precipitating flaw within a laser shock peened area of the test piece that was laser shock peened in the same or similar laser shock peening apparatus.
4. A method as claimed in claim 1 wherein the acoustic energy parameter values are maximum amplitudes of corresponding ones of the signals during the duration of each corresponding one of the plasmas.
5. A method as claimed in claim 4 wherein the statistical function value is an average of the acoustic energy parameter values for the laser beam pulses.
6. A method as claimed in claim 5 wherein the pass or fail criteria is based on a pre-determined correlation of test piece statistical function data and high cycle fatigue failure based on high cycle fatigue tests of test pieces that were laser shock peened in the same or similar laser shock peening apparatus.
7. A method as claimed in claim 6 wherein the test pieces each have a failure precipitating flaw within a laser shock peened area of the test piece that was laser shock peened in the same or similar laser shock peening apparatus.
8. A method as claimed in claim 1 wherein the acoustic energy parameter values are the signals integrated over time of the period of the duration of each corresponding one of the plasmas.
9. A method as claimed in claim 8 wherein the statistical function value is an average of the acoustic energy parameter values for the laser beam pulses.
10. A method as claimed in claim 9 wherein the pass or fail criteria is based on a pre-determined correlation of test piece statistical function data and high cycle fatigue failure based on high cycle fatigue tests of test pieces that were laser shock peened in the same or similar laser shock peening apparatus.
11. A method as claimed in claim 10 wherein the test pieces each have a failure precipitating flaw within a laser shock peened area of the test piece that was laser shock peened in the same or similar laser shock peening apparatus.
12. A method as claimed in claim 1 wherein:
first and second acoustic energy parameter values for each of the acoustic signals are calculated,
first and second statistical functions based on the first and second acoustic energy parameter values are calculated, and
the first and second statistical function values are compared to first and second pass or fail criteria respectively for quality assurance of the laser shock peening process for accepting or rejecting the workpiece.
13. A method as claimed in claim 12 wherein first and second acoustic energy parameter values for each of the acoustic signals are maximum amplitudes of corresponding ones of the signals during the duration of each correspond- ing one of the plasmas and signals integrated over time of the period of the duration of corresponding ones of each corresponding one of the plasmas.

14. A method as claimed in claim 13 wherein the statistical function value is based on first and second averages of the first and second acoustic energy parameter values respectively for the laser beam pulses.

15. A method as claimed in claim 14 wherein the pass or fail criteria is based on a pre-determined correlation of test piece statistical function data and high cycle fatigue failure based on high cycle fatigue tests of test pieces that were laser shock peened in the same or similar laser shock peening apparatus.

16. A method as claimed in claim 15 wherein the test pieces each have a failure precipitating flaw within a laser shock peened area of the test piece that was laser shock peened in the same or similar laser shock peening apparatus.

17. A method as claimed in claim 1 wherein the acoustic signals are measured with an acoustic transducer mounted to the workpiece.

18. A method as claimed in claim 17 wherein the pass or fail criteria is based on a pre-determined correlation of test piece statistical function data and high cycle fatigue failure based on high cycle fatigue tests of test pieces that were laser shock peened in the same or similar laser shock peening apparatus.

19. A method as claimed in claim 18 wherein the test pieces each have a failure precipitating flaw within a laser shock peened area of the test piece that was laser shock peened in the same or similar laser shock peening apparatus.

20. A method as claimed in claim 17 wherein the acoustic energy parameter values are maximum amplitudes of corresponding ones of the signals during the duration of each corresponding one of the plasmas.

21. A method as claimed in claim 20 wherein the statistical function value is an average of the acoustic energy parameter values for the laser beam pulses.

22. A method as claimed in claim 17 wherein the acoustic energy parameter values are the signals integrated over time of the period of the duration of each corresponding one of the plasmas.

23. A method as claimed in claim 22 wherein the statistical function value is an average of the acoustic energy parameter values for the laser beam pulses.

24. A method as claimed in claim 17 wherein:
   first and second acoustic energy parameter values for each of the acoustic signals are calculated,
   first and second statistical functions based on the first and second acoustic energy parameter values are calculated, and
   the first and second statistical function values are compared to first and second pass or fail criteria respectively for quality assurance of the laser shock peening process for accepting or rejecting the workpiece.

25. A method as claimed in claim 24 wherein first and second acoustic energy parameter values for each of the acoustic signals are maximum amplitudes of corresponding ones of the signals during the duration of each corresponding one of the plasmas and signals integrated over time of a period of the duration of corresponding ones of the plasmas respectively.

26. A method as claimed in claim 25 wherein the statistical function value is based on first and second averages of the first and second acoustic energy parameter values respectively for the laser beam pulses.

27. A method as claimed in claim 26 wherein the pass or fail criteria is based on a pre-determined correlation of test piece statistical function data and high cycle fatigue failure based on high cycle fatigue tests of test pieces that were laser shock peened in the same or similar laser shock peening apparatus.

28. A method as claimed in claim 27 wherein the test pieces each have a failure precipitating flaw within a laser shock peened area of the test piece that was laser shock peened in the same or similar laser shock peening apparatus.

29. A method as claimed in claim 28 wherein the workpiece is an airfoil of gas turbine engine blade or vane.

30. A method as claimed in claim 17 wherein the workpiece is an airfoil of gas turbine engine blade or vane.

31. A method for quality control testing of a laser shock peening process of production workpieces, said method comprising the following steps:
   (a) laser shock peening a surface of the production workpiece by firing a plurality of laser beam pulses from a laser shock peening apparatus on a surface of the production workpiece and forming a plurality of corresponding plasmas, each one of the plasmas for each one of the pulses having a duration in which the plasma causes a region to form beneath the surface, the region having deep compressive residual stresses imparted by the laser shock peening process,
   (b) measuring airborne and workpiece-borne acoustic signals for each of the laser beam pulses during a period of time during the duration of each corresponding one of the plasmas, wherein the workpiece-borne acoustic signal is measured with an acoustic transducer mounted to the workpiece which detects acoustic signals though the workpiece and the airborne acoustic signal is measured with a microphone spaced located away from the workpiece and which detects airborne acoustic signals,
   (c) calculating airborne and workpiece-borne acoustic energy parameter values for each of the corresponding acoustic signals,
   (d) calculating airborne and workpiece-borne statistical function values of the workpiece based on the acoustic energy parameter values, and
   (e) comparing the airborne and workpiece-borne statistical function values to corresponding pass or fail criteria for quality assurance of the laser shock peening process for accepting or rejecting the workpiece.

32. A method as claimed in claim 31 wherein the airborne and workpiece-borne acoustic energy parameter values are maximum amplitudes of corresponding ones of the workpiece-borne and the airborne acoustic signals during the duration of each corresponding one of the plasmas.

33. A method as claimed in claim 32 wherein the airborne and workpiece-borne statistical function values are averages of the corresponding ones of the workpiece-borne and the airborne acoustic energy parameter values for the laser beam pulses.

34. A method as claimed in claim 31 wherein the airborne and workpiece-borne acoustic energy parameter values are the airborne and workpiece-borne acoustic signals integrated over time of the period of the duration of corresponding ones of the signals during the duration of each corresponding one of the plasmas.

35. A method as claimed in claim 34 wherein the airborne and workpiece-borne statistical function values are averages of the corresponding ones of the workpiece-borne and the airborne acoustic energy parameter values for the laser beam pulses.

36. A method as claimed in claim 31 wherein:
   first and second acoustic energy parameter values for each of the workpiece-borne and the airborne acoustic signals are calculated, first and second statistical functions are calculated for each of the workpiece-borne and the airborne acoustic signals based on the first and second acoustic energy parameter values, and the first and second workpiece-borne and airborne statistical function values are compared to first and second workpiece-borne and the airborne pass or fail criteria respectively for quality assurance of the laser shock peening process for accepting or rejecting the workpiece.

37. A method as claimed in claim 36 wherein first and second acoustic energy parameter values for each of the acoustic signals are maximum amplitudes of corresponding ones of the signals during the duration of each corresponding one of the plasmas and signals integrated over time of the period of the duration of corresponding ones of the signals during the duration of each corresponding one of the plasmas respectively.

38. A method as claimed in claim 37 wherein the first and second workpiece-borne and airborne statistical function values are based on first and second workpiece-borne and airborne averages of the first and second workpiece-borne and airborne acoustic energy parameter values respectively for the laser beam pulses.

39. A method as claimed in claim 38 wherein the pass or fail criteria is based on a pre-determined correlation of test piece first and second workpiece-borne and airborne statistical function data and high cycle fatigue failure based on high cycle fatigue tests of test pieces that were laser shock peened in the same or similar laser shock peening apparatus.

40. A method as claimed in claim 39 wherein the test pieces each have a failure precipitating flaw within a laser shock peened area of the test piece that was laser shock peened in the same or similar laser shock peening apparatus.

41. A method as claimed in claim 40 wherein the workpiece is an airfoil of gas turbine engine blade or vane.

* * * * *